United States Patent
Hübschen

(10) Patent No.: US 6,766,694 B2
(45) Date of Patent: Jul. 27, 2004

(54) ELECTROMAGNETIC ULTRASONIC TRANSDUCER

(75) Inventor: Gerhard Hübschen, Saarlouis (DE)

(73) Assignee: Fraunhofer-Gesellschaft zur Forderung der angewandten Forschung e.V., Munich (DE)

( * ) Notice: Subject to any disclaimer, the term of this patent is extended or adjusted under 35 U.S.C. 154(b) by 0 days.

(21) Appl. No.: 10/332,132

(22) PCT Filed: Jul. 5, 2001

(86) PCT No.: PCT/DE01/02544
§ 371 (c)(1),
(2), (4) Date: Jan. 6, 2003

(87) PCT Pub. No.: WO02/04135
PCT Pub. Date: Jan. 17, 2002

(65) Prior Publication Data
US 2003/0159516 A1 Aug. 28, 2003

(30) Foreign Application Priority Data
Jul. 7, 2000 (DE) .......... 100 33 228

(51) Int. Cl.⁷ ............ G01N 29/24
(52) U.S. Cl. .......... 73/643
(58) Field of Search ............ 73/643, 629

(56) References Cited

U.S. PATENT DOCUMENTS 4,232,557 A * 11/1980 Vasile .......... 73/643
5,608,164 A * 3/1997 MacLauchlan .......... 73/643

FOREIGN PATENT DOCUMENTS

DE 3637366 * 5/1988

* cited by examiner

Primary Examiner—John E. Chapman
(74) Attorney, Agent, or Firm—Breiner & Breiner, L.L.C.

(57) ABSTRACT

The present invention relates to an electromagnetic ultrasonic transducer for generating horizontally polarized transverse waves. The transducer comprises a coil support (4) which is made of a material having good magnetic conductivity and which is provided with a comb-like structure having parallel running channels (5) and fins (6). A plurality of HF coils (1) which are electrically interconnected in series are wound on at least some of said fins 6 at some distance the faces of said fins (6) with adjacent coils (1) having an alternating direction of wind. In the channels (5) are arranged a plurality of rows (3) of permanent magnets (2) having alternating pole assignment.

With the present ultrasonic transducer, in particular low-frequency SH waves can be generated in or receiving out of electrically conductive materials without the risk of wearing the HF coils.

9 Claims, 4 Drawing Sheets

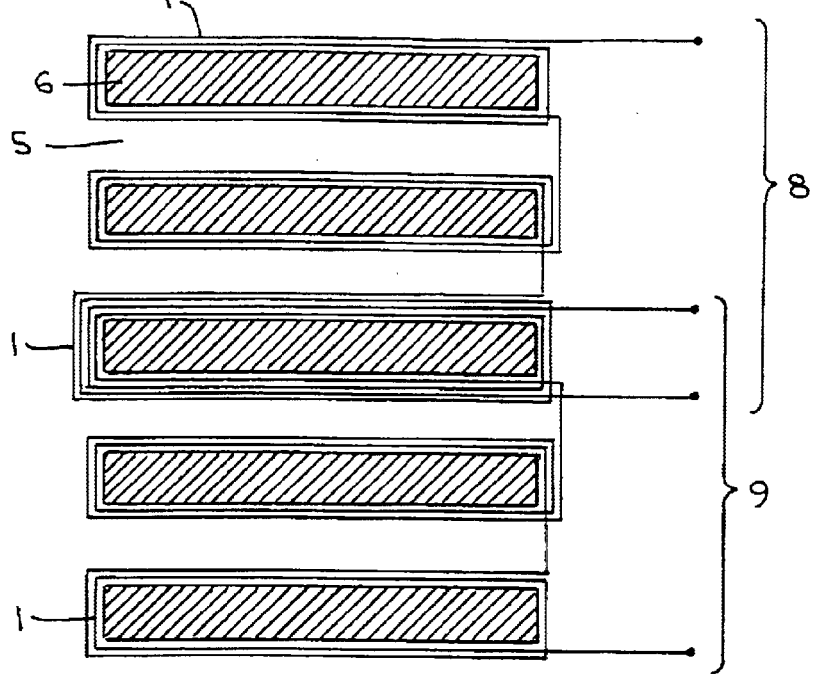
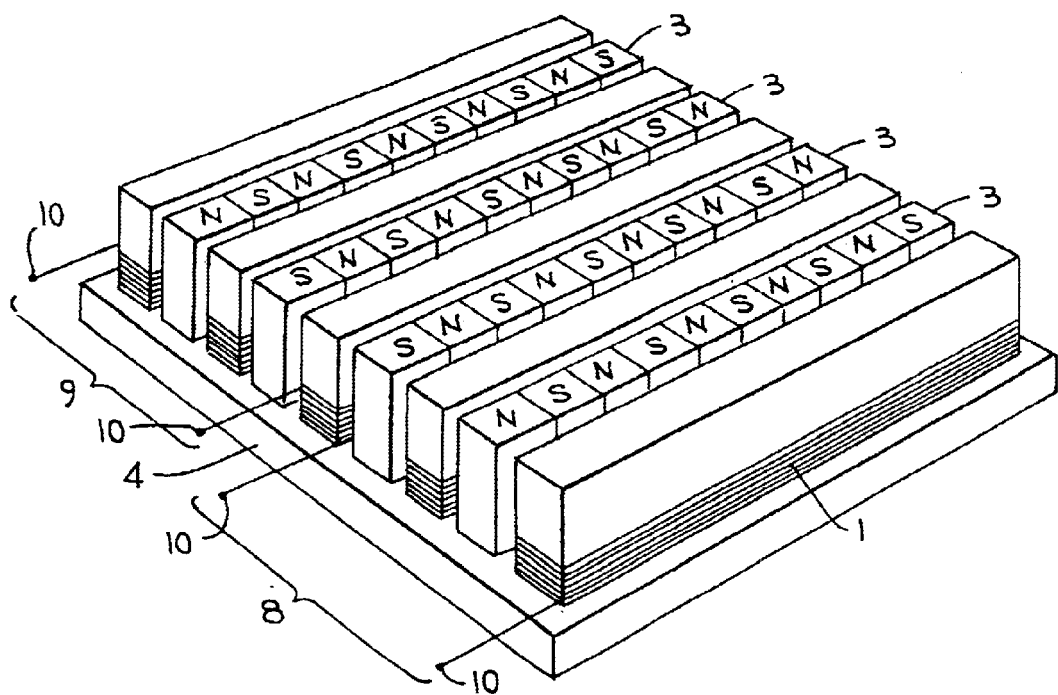

ELECTROMAGNETIC ULTRASONIC TRANSDUCER

The present invention relates to an electromagnetic ultrasonic transducer for impinging ultrasonic waves upon a work piece which is made of an electrically-conductive material or for receiving ultrasonic waves. The transducer comprises a coil support, which is made of a material having good magnetic-conductivity and which has a comb-like structure having parallel running channels and fins as well as HF coils, which are electrically interconnected in series and which are wound onto at least some of the fins at a distance from the radiation side of the transducer formed by the faces of the fins and in such a manner that the adjacent coils have an alternating direction of wind. Furthermore, the ultrasonic transducer has means for generating a static magnetic field.

In using such a transducer, for example, for nondestructive testing of electrically conductive or ferromagnetic work pieces for internal and surface faults, the transducer is placed with its radiation side in the vicinity of the surface of the to-be-tested work piece. Applying a high-frequency current to the HF coils of the transducer induces eddy currents in the work piece. These eddy current lead, under the influence of the magnetic field, to propagation of the ultrasonic waves in the work piece. In the same manner, such a transducer can receive ultrasonic waves reflected at faults in the work piece and convert them into high-frequency current pulses. This can occur using the same HF coils or using a separate set of coils. Due to the noncontact generation of ultrasonic waves in the work piece, such transducers offer particular advantages in testing work pieces in motion.

STATE OF THE ART

In the prior art embodiments of electromagnetic ultrasonic transducers, there is a difference between transducers that generate polarized transverse waves, so-called SV waves (shear vertical waves), in the plane of incidence and transducers that generate horizontally polarized transverse waves, so-called shear horizontal waves (SH waves), in the work piece or receive such shear horizontal waves from the work piece. The type of generation differs in both cases essentially in the kind and direction of the magnetic field which acts on the eddy current induced by the HF coils.

For instance, DE 36 37 366 A1 discloses an electromagnetic ultrasonic transducer for generating vertically polarized transverse waves (SV waves) provided with a coil support having a comb-like structure with parallel running channels and fins on which a plurality of HF coils, which are interconnected in series, are wound in alternating wind direction. By maintaining a minimum distance between the coil windings and the fin faces forming the radiation side of the transducer, the HF coils are protected from damage due to coming into contact with the to-be-tested work piece. In order to generate the required magnetic field, a permanent magnet or an electromagnet is disposed over the comb-like coil support. This magnet supplies a homogeneous static magnetic field in the region of the surface of the work piece.

The transducer periodicity of such an electro-magnetic ultrasonic transducer is determined by the distance between the single fins of the comb structure and the type of winding of the HF coil. Half the transducer periodicity corresponds to the distance between adjacent fins. Sound radiation occurs perpendicular to the fins of the coil support.

DE 36 37 366 A1 also discloses a preferred embodiment of an ultrasonic transducer in which the generated magnetic field is directed parallel to the longitudinal side of the fin and parallel to the surface of the work piece in order to generate transverse waves (SH waves) polarized perpendicular to the plane of incidence. In such a case, generating the ultrasonic waves in the work piece occurs via a purely magnetostriction mechanism. In this case, the magnetic field is aligned parallel to the eddy currents induced in the work piece. The disadvantage of this method of generation is, however, that generation effectiveness and reception amplitude are strongly dependent on the mechanical and metallurgical properties of the surface of the work piece. Furthermore, this type of generation requires that the work piece be made of a ferromagnetic material.

In order to avoid these problems, transducers with a periodic permanent magnet arrangement, in which the magnetic field is essentially directed perpendicular to the surface of the work piece, are used for ultrasonic generation of horizontally polarized transverse waves (SH waves). Prior art transducers comprise two rows of permanent magnets, on the radiation side of which a rectangular coil is wound. Such an assembly, as is shown by way of example schematically in FIG. 1, generates particle excursions in electrically conductive work piece materials when HF currents are applied to the coils due to the Lorentz force acting on the eddy currents induced in the surface of the work piece as a result of the magnetic field. These particle excursions lead to the generation of SH waves.

A further improvement of this type of transducer for generating polarized transverse waves perpendicular to the plane of incidence is disclosed in EP 0 609 754 A2. In this embodiment, at least four rows of alternating permanent magnet segments are provided, with two adjacent rows staggered a quarter of the periodicity of the single permanent magnets of each row respectively along their longitudinal axis. Each adjacent permanent magnet arrangement is provided with its own high-frequency coil. These high-frequency coils can be impinged with a HF signal shifted 90° between the two high-frequency coils. In this manner, it is achieved that this ultrasonic transducer, both as transmitter transducer and receiver transducer, is provided with a one-sided direction characteristic with a single main radiation direction so that an improved signal/noise ratio is yielded in the nondestructive testing of the work piece.

However, when using such electromagnetic ultrasonic transducers, the sensitive coil wires lie between the permanent magnets and the surface of the work piece. As the coils must be placed very closely to the surface of the work piece in testing of the work piece in order to generate the ultrasonic amplitudes required for sufficient signal/noise ratio, there is greater risk of damaging and wearing the HF coils. Effective protection against wearing these coils is very difficult to realize in these transducers, because a protective covering would lead to undesired dampening of the amplitudes.

DE 42 23 470 discloses another electromagnetic ultrasonic transducer for generating high-frequency SH waves. This transducer comprises a toroidal strip core on which the windings of the HF coil are disposed at a distance from the faces, i.e. at a distance from the surface of the work piece, which reduces the risk of damaging or wearing the windings when using the transducer. This principle using toroidal strip cores is, however, not suited for setting up low-frequency SH wave transducers with large aperture widths, because only little generation effectiveness can be achieved.

Based on this state of the art, the object of the present invention is to provide an electromagnetic ultrasonic transducer for generating horizontally polarized transverse waves (SH waves), which are in particular also suited for the low-frequency SH wave range and permits testing work pieces made of electrically conducting materials with little risk of wearing for the HF coils.

DESCRIPTION OF THE INVENTION

The object of the present invention is solved using the electromagnetic ultrasonic transducer according to the claims. Advantageous embodiments of the electromagnetic ultrasonic transducer are the subject matter of the subclaims.

The present ultrasonic transducer comprises a coil support made of a material having good magnetic conductivity, i.e. a highly permeable material, which is provided with a comb-like structure having at least almost parallel running channels and fins as well as a plurality of HF coils which are electrically interconnected in series and are wound on at least some of the fins at a distance from a radiation side, which is formed by the faces of the fins, of the transducer in such a manner that the adjacent coils have an alternating wind direction. The radiation side corresponds in this transducer, as in the prior art transducers of the cited state of the art, to the bottom side of the transducer facing the work piece during testing. Furthermore, the transducer comprises a plurality of rows of permanent magnets which are disposed in the channels of the transducer in the longitudinal direction of the fins and have an alternating polar assignment.

The present electromagnetic ultrasonic transducer, referred to in the following also as electromagnetic SH wave transducer, is particularly suited for ultrasonic testing electrically conductive or ferromagnetic materials. Due to the special design of the core material, i.e. the coil support and the corresponding arrangement of the permanent magnets, the highly sensitive wires of the HF coils are raised a few millimeters from the surface of the to-be-tested work piece. The distance between the coil windings and the face of the fins, which form the bottom side respectively the radiation side of the transducers, is preferably about 6 to 8 mm. In this manner, the disadvantage of having to place the sensitive HF coils very proximate to the surface of the work piece in order to effectively protect the transducer against wear is avoided. The present transducer can be used particularly for generating low-frequency SH waves.

Contrary to the transducer periodicity of the transducer of DE 36 37 366 A1, the transducer periodicity is not determined by the distance between two adjacent fins of the coil support but rather by the periodicity of the arrangement of the magnets, i.e. by the (center of gravity) distance respectively the length of the single permanent magnets of a row of permanent magnets, with the length referring to the dimension in the longitudinal direction of the fin. The wave length projected on the surface of the workpiece and thus also the periodicity of the transducer is therefore oriented parallel to the channels respectively the fins of the coil support.

In the present transducer, the HF coils themselves are wound about the individual fins, with the wind direction of the HF coils of adjacent fins alternating. The electrical connection of these coils yields a coil arrangement course, which the cited state of the art also refers to as meandering, over the entire radiation surface of the transducer.

Due to the HF coils, which are electrically interconnected in series, of the single fins, dynamic magnet fields are impressed in the material of the to-be-tested work piece. These dynamic magnetic fields generate eddy currents therein. In the present transducers, these eddy currents run essentially under the permanent magnets, which have alternating pole assignment, in the direction of the channels of the comb. The permanent magnets generate a spatially periodic magnetic field essentially perpendicular to the surface of the work piece. In the adjacent channels, the current direction runs in the opposite direction. Due to the charge movement perpendicular to the magnetic field, the Lorentz forces act leading to particle excursions at the surface of the work piece and thus to the radiation of horizontally polarized transverse waves in the direction of the channels of the comb-like coil support. In a preferred embodiment in which pole assignment of the permanent magnets changes in the adjacent channels, acting-in-the-same-direction Lorentz forces act transverse to the parallel direction of the channels and fins.

In contrast to the transducer of DE 36 37 366 A1, in the present transducer the sonic radiation direction is oriented parallel to the fins respectively to the channels of the comb structure. Furthermore, the present transducer is based on the Lorentz principle, whereas in operation the DE 36 37 366 A1 wave transducer acts as a SH wave transducer via a pure magnetostriction mechanism. Due to the utilization of Lorentz forces in generating ultrasonic waves with the present transducer, ultrasound generation is substantially less dependent on the properties of the material than the SH wave transducer of DE 36 37 366 A1. Furthermore, not only ferromagnetic materials, but also all other electrically conductive materials can be tested with the present transducer.

Of course, the present transducer can be operated not only as a transmitter transducer in which the HF coils are fed HF current from a high-frequency generator. But rather the transducer is also suited to receive ultrasonic waves in reverse direction in the work piece with the same coil system and to pass the respective high-frequency signals on to an evaluation unit via the HF coils. In the same manner, different coil systems for transmitting and receiving ultrasonic waves can also be provided on the same comb-like support. In the latter case, the HF coils for receiving ultrasonic waves preferably have twice the number of coil windings than the HF coils for generating ultrasonic waves.

Further details on generating and receiving ultrasonic waves using such a type of electromagnetic ultrasonic transducer, also referred to as an electrodynamic ultrasonic transducer, are not described because they are familiar to someone skilled in the art from DE 36 37 366 A1 or EP 0 609 754 A2.

In one preferred embodiment of the present ultrasonic transducer, in which the permanent magnets of the rows of permanent magnets of adjacent channels are disposed on the same level, i.e. at the same distance to a line perpendicular to the channels respectively the fins, two-sided sound radiation is realized which can be of use in certain applications. However, by means of a special arrangement of the permanent magnets respectively of rows of permanent magnets, also one-sided sound radiation can be realized by an invented ultrasonic transducer in which the adjacent rows of permanent magnets are disposed shifted half the width of a magnet respectively in relation to a base line running perpendicular to the channel. In addition, two separate HF coil arrangements are employed with which one half of the fins of the coil support is impinged. As in this embodiment the permanent magnets of the adjacent channels are spatially staggered $\lambda/4$ of a transducer periodicity, a phase difference of 180° of the signals, i.e. erasure of the signals, in one radiation respectively one reception direction of the transducer and structural overlapping in the other radiation direction are the result. This leads to a one-sided radiation characteristic respectively a one-sided reception characteristic of the transducer.

In another advantageous embodiment of the present transducer, one half of the fins are wound with a coil arrangement, the other half with a coil arrangement which can be separately triggered. The permanent magnets in each channel of a coil arrangement are alternately poled in the direction perpendicular to the channels. The same applies to the permanent magnets of the other coil arrangement, however in the middle of the coil support two adjacent rows of magnets have the same pole assignment in a direction perpendicular to the channels. Both coil arrangements are connected to the inputs of a differential amplifier, with the reception signals of the coils possessing a phase difference of 180°. In this manner, a reception transducer is realized in differential technology.

The number of fins and channels of the coil support of the present ultrasonic transducer can be selected as desired. However, at least three fins should be provided so that two rows of permanent magnets are disposed parallel to each other. In an embodiment for generating a one-sided directional characteristic, at least five should be provided so that there are four parallel rows of permanent magnets. The material of the coil support should have good magnetic conductivity, i.e. be highly permeable and possess poor electrical conductivity. The width of the fins may correspond about to the width of the rows of permanent magnets. The same applies to the height of the fins. Of course, the height of the permanent magnets can also be less or a bit greater than the height of the fins as long as generation of the ultrasonic waves in the work piece is still ensured by the Lorentz forces. The periodicity of the ultrasonic transducer is determined by the length of the single permanent magnets so that someone skilled in the art determines the length as suited according to the desired transducer periodicity. The aperture width of the transducer is determined by the area over which the fins and the permanent magnets disposed in channels extend and is also selected according to the intended application.

Of course, the geometric shape of the fins and of the channels is not limited to a rectangular cross section. But rather the shape of these fins and channels may deviate from a rectangular cross section without impairing the function of the present transducer. The coil windings wound on the fins are preferably provided with an insulation coat in order to prevent an electric short circuit.

BRIEF DESCRIPTION OF THE DRAWINGS

The present electromagnetic ultrasonic transducer is briefly described again in the following using preferred embodiments with reference to the drawings without the intention of limiting the overall inventive idea.

FIG. 5 shows the winding scheme of the ultrasonic transducer of FIG. 4;

FIG. 6 shows a third preferred embodiment of an electro-magnetic ultrasonic transducer according to the present invention;

WAYS TO CARRY OUT THE INVENTION

Figure 1:
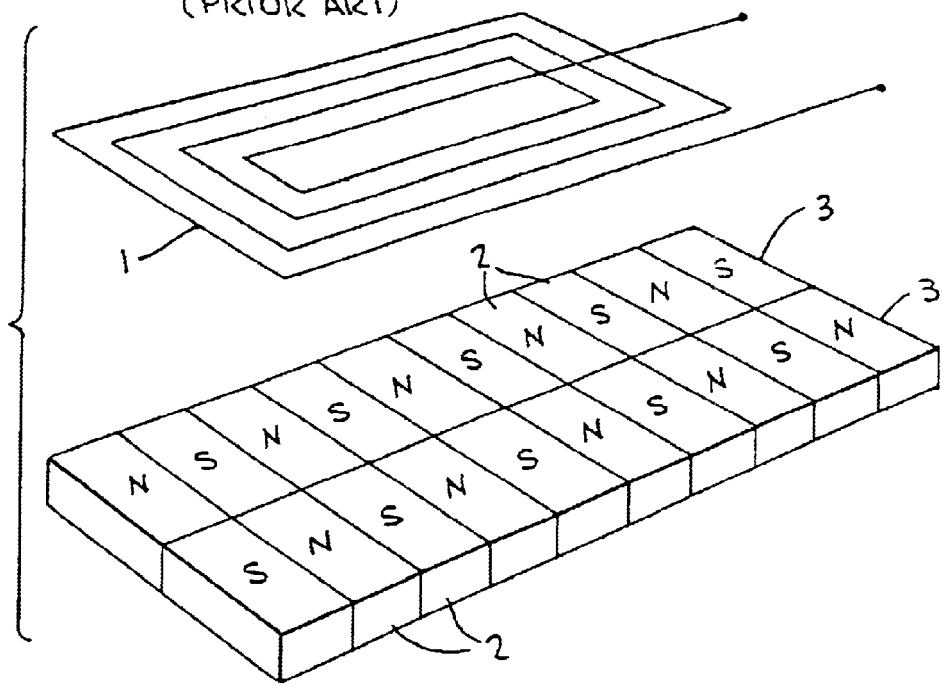
FIG. 1 shows an example of an electromagnetic ultrasonic transducer for generating horizontally polarized transverse waves according to the state of the art.

FIG. 1 shows an example of an electromagnetic ultrasonic transducer for state-of-the-art ultrasonic generation of horizontally polarized transverse waves (SH waves). In this transducer, the magnet arrangement is composed of two rows of permanent magnets 2 whose pole assignment alternates both in the direction of the row of magnets 3 and perpendicular to this direction. A HF coil 1 which is designed as a rectangular coil, for better illustration drawn spatially separate from the permanent magnets 2, is disposed on the bottom of this permanent magnet arrangement. When HF currents are applied to this HF coil 1, the action of the Lorentz forces caused by the magnetic field created in electrically conductive materials by the permanent magnets 2 leads to particle excursions which generate SH waves in the work piece. However, in order to generate a sufficiently high amplitude of these ultrasonic waves, the electromagnetic ultrasonic transducer must be placed very close to the bottom side of the surface of the work piece shown in the figure. Therefore, such a type of transducer harbors the risk of damage to the HF coil 1 disposed on the bottom side during testing of the work piece.

Figure 2:
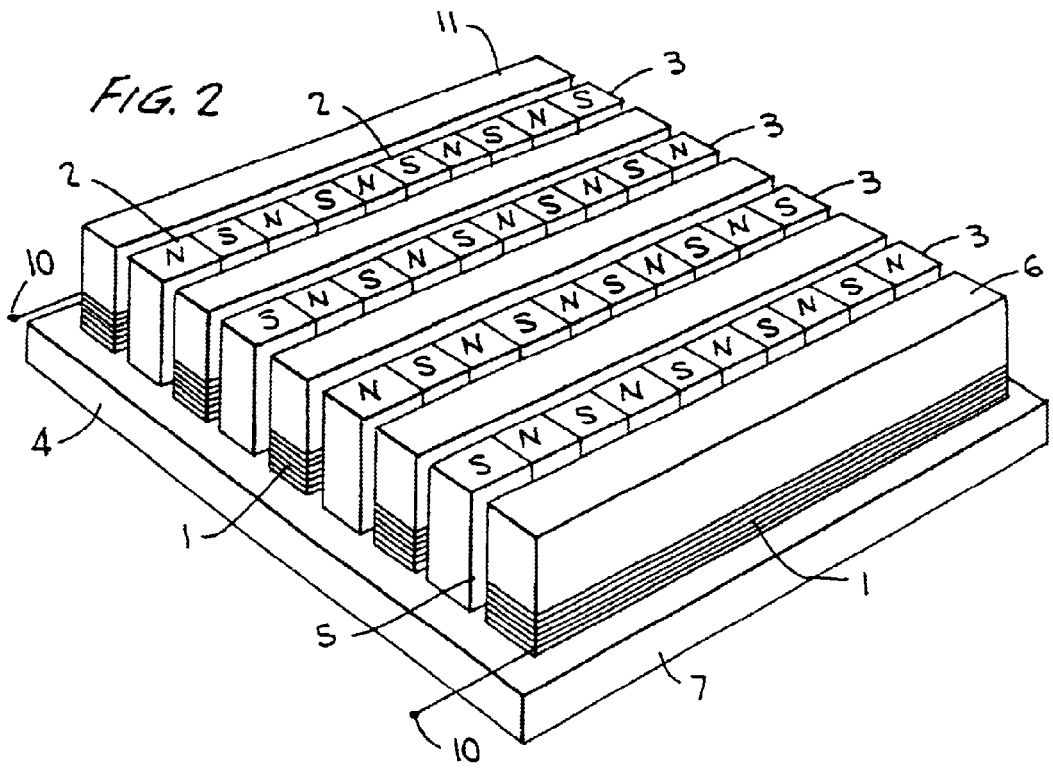
FIG. 2 shows a first preferred embodiment of an electro-magnetic ultrasonic transducer according to the present invention.

To avoid this problem, the present ultrasonic transducer is proposed which is depicted in a preferred embodiment in FIG. 2. FIG. 2 again shows a top view of the bottom side respectively the radiation side of such an electromagnetic ultrasonic transducer. In this example, the ultrasonic transducer comprises a coil support 4 having five parallel running fins 6 having channels 5 which are disposed on a base plate 7 lying between them. In this case, the coil support 4 is made of a ferromagnetic material. Furthermore, the transducer is provided with five HF coils 1, which are interconnected in series. Each of the coils 1 is wound on one of the fins 6, as the figure shows. The wind direction of the coils 1 alternates from coil to coil respectively from fin to fin in such a manner that the direction of the currents flowing through the coil windings alternates from channel to channel. When this transducer is in operation, the two connections 10 of the HF coil arrangement shown in the figure are connected to a high-frequency generator which impinges the HF coils 1 with electrical high-frequency impulses. In the reception case, these connections 10 are connected to an evaluation unit which evaluates the signals received via the HF coils 1.

In the present ultrasonic transducer, small permanent magnets 2 with alternating pole assignment are disposed in the intermediate spaces formed by the channels 5 between the parallel running fins 6 in such a manner that a row of permanent magnets 3 is formed in each channel 5. The pole assignment alternates both within the single channels 5 as well as perpendicular to the longitudinal direction of the fins 6, from channel to channel, as FIG. 2 clearly shows. Furthermore, FIG. 2 shows that the coil windings of the HF coils 1 are wound on the fins 6 at a distance from the face of the fins 6 respectively from the bottom side of the transducer. In this manner, the disadvantage of having to dispose the sensitive HF coils very close to the to-be-tested surface of the work piece is avoided. But rather, the sensitive coils are protected by the respective fins 6 themselves and by the permanent magnets 2.

In the transducer of the present invention, the width of the rows of magnets is preferably 2 to 3 mm independent of the present preferred embodiment. If a frequency of, for example, 1.4 MHz from the HF generator is applied to the HF coil arrangement, a radiation angle of about 55° to the plane formed by the bottom side of the transducer can be achieved. If the frequency of the feed signal is altered down to 1 Mhz, the radiation angle of the ultrasonic signal can be shifted down to that of incidental sound radiation. The height of the fins 6 and the rows of permanent magnets 3 is preferably between 6 and 10 mm and the coil windings of the HF coils 1 are preferably at a distance of about 6 to 8 mm from the face 11 of the fins. The width of the channels 5 between the individual fins 6 and the width of the fins 6 may be in the range between 4 and 10 mm. These dimensions, which are given as examples, apply for all the preferred embodiments of the invented transducer.

The transducer shown as an example in the figure is particularly suited for generating low-frequency SH waves. The wave length projected on the surface of the work piece (periodicity of this transducer) is determined by the periodicity of the magnet arrangement. The sound radiation direction is oriented parallel to the fins 6 and the channels 5 of the comb structure.

Figure 3:
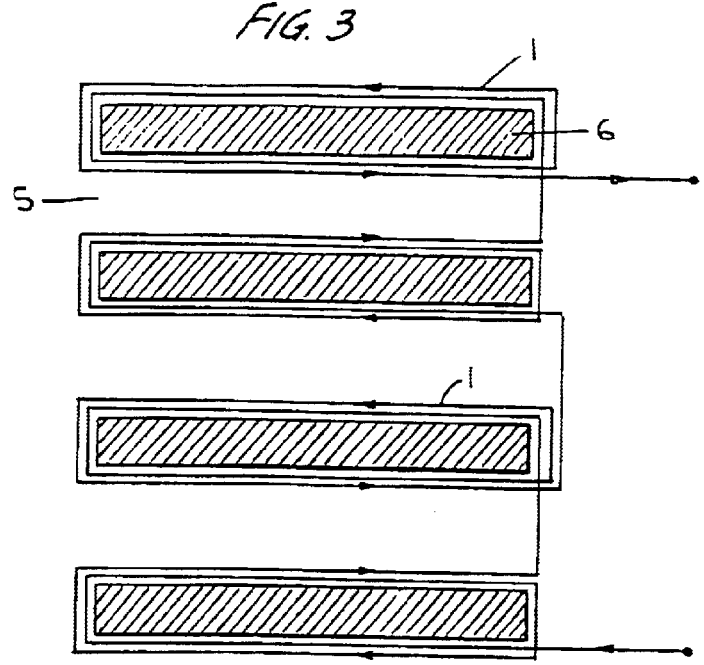
FIG. 3 shows the winding scheme of the ultrasonic transducer of FIG. 2.

FIG. 3 shows schematically in a vertical top view of the bottom side the winding scheme of an electromagnetic SH wave transducer like the one in FIG. 2. In the figure, the fins 6, here all told four fins, and the channels 5 lying between them are only sketched in. As the figure shows, the single HF coils 1 are wound on the fins 6 and the wind direction alternates respectively changes from fin to fin. In this manner, as a result of the coil windings being adjacent to the channels 5, a current direction, indicated in the figure by an arrow, is yielded which changes from channel to channel.

Figure 4:
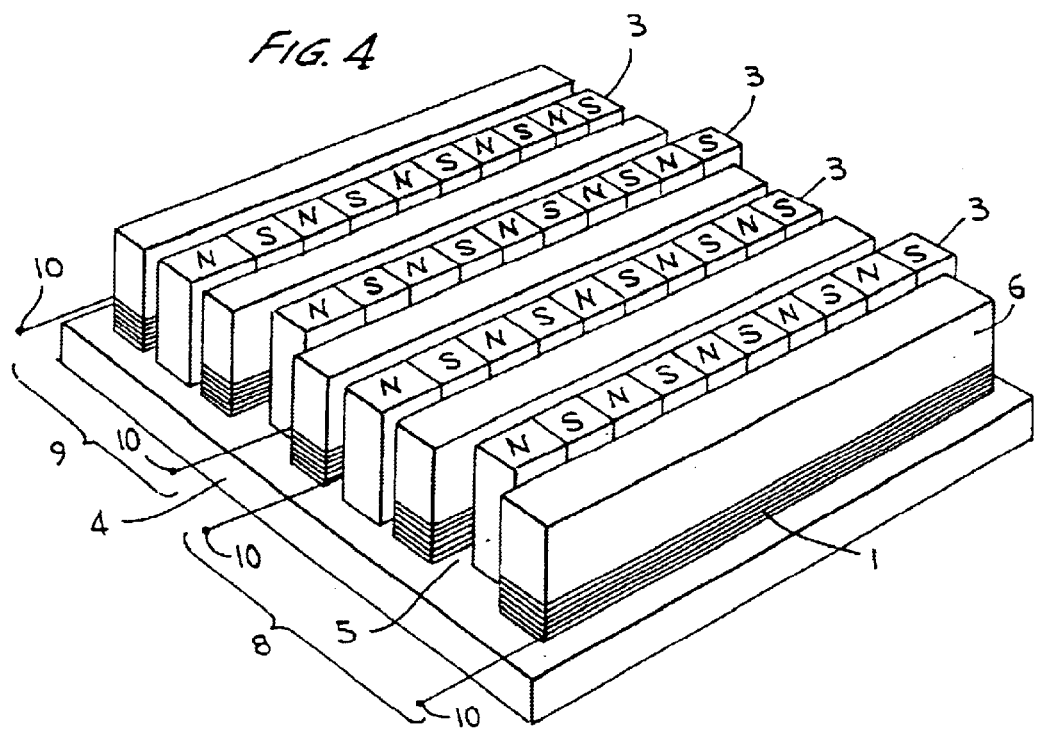
FIG. 4 shows a second preferred embodiment of an electro-magnetic ultrasonic transducer according to the present invention.

FIG. 4 shows another preferred embodiment of an electromagnetic ultrasonic transducer according to the present invention. In this transducer, the coil support with the fins 6 and channels 5 is designed in the same manner as the preferred embodiment of FIG. 2. Contrary to the preferred embodiment of FIG. 2, in the present transducer two separate groups of HF coils 1 are wound on the coil support 4. The first group of HF coils 1 electrically interconnected in series, referred to as the first arrangement of HF coils 8 in the following, is wound on the right three fins 6 in the figure and the wind direction of the HF coils 1 again alternates from fin to fin. Another group of HF coils 1, referred to as the second arrangement 9 of HF coils, is wound in the same manner on the left three fins 6, i.e. with alternating wind directions from fin to fin. Thus, windings of both HF coil arrangements 8, 9 are placed around the middle fin. Both HF coil arrangements 8, 9 have separate connections 10 respectively as the figure shows.

The rows 3 of permanent magnets having alternating pole assignments are disposed in the channels 5 between the fins 6. In this example, the rows 3 of permanent magnets are staggered about half the width of a magnet from channel to channel, which corresponds to staggering the transducer periodicity by λ/4. The staggering relates to a line perpendicular to the fins 6 of the coil support 4 permanent magnets.

In such a transducer, applying 90° staggered current signals to the two HF coil arrangements 8, 9 yields a signal phase difference of 180° in the radiation direction, i.e. an erasure of the signals and, in the other radiation direction, structural overlapping of the generated ultrasonic waves. In this manner, one-sided sound radiation of the ultrasonic transducer is achieved.

FIG. 5 shows once again in a vertical top view of the bottom side of a transducer as in FIG. 4, the course of the coil windings wound on the fins 6 with the current direction indicated by the arrows.

FIG. 6 shows another preferred embodiment of an electromagnetic ultrasonic transducer according to the present invention. The design of the coil support 4 with the channels 5 and the fins 6 corresponds again to the preceding preferred embodiments. In this example, too, as in the preferred embodiment of FIG. 4, two separately triggerable HF coil arrangements 8 and 9 are wound on the fins 6 according to the description of FIG. 4.

In the present preferred embodiment, the rows 3 of permanent magnets 3 having alternating pole assignment are disposed in channel 5 in such a manner that the pole assignment alternates in the two halves, i.e. in the two right and in the two left channels 5 of the figure in the direction perpendicular to the fins 6. However, in the middle of the coil support 4 two adjacent rows 3 of permanent magnets have the same pole assignment. Contrary to the preferred embodiment of FIG. 4, the individual rows 3 of permanent magnets are not staggered.

Such an ultrasonic transducer can be operated as a reception transducer in differential technology. In this case, the two HF coil arrangements 8, 9 are connected to a differential amplifier, not depicted in the figure, with the reception signals of the coils having a phase difference of 180° due to the described arrangement of the permanent magnets.

Figure 7:
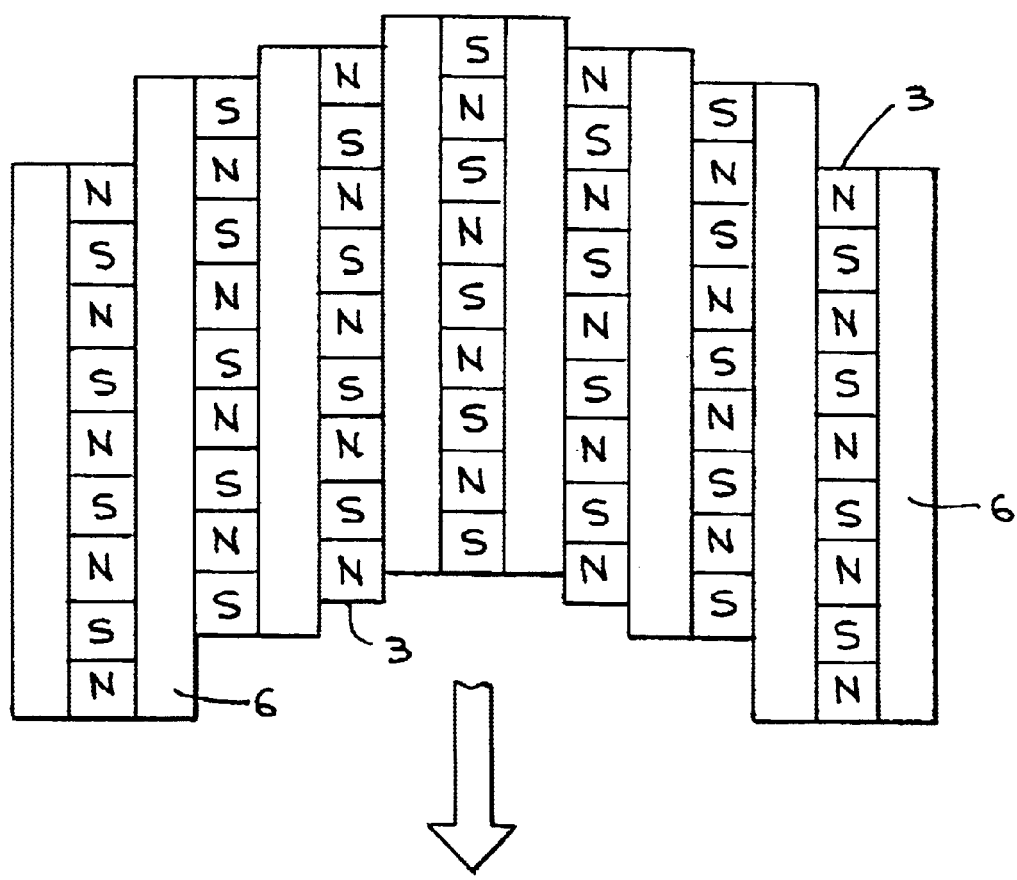
FIG. 7 shows a fourth preferred embodiment of an electro-magnetic ultrasonic transducer according to the present invention.

FIG. 7 shows a top view of the bottom side of another preferred embodiment of an electromagnetic ultrasonic transducer according to the present invention. The HF coils are not depicted in this figure. However, they can be wound on the fins 6 in the same manner as in the preferred embodiments described in the preceding.

In this preferred embodiment, both the fins 6 and the rows 3 of the permanent magnets 2 are staggered in the longitudinal direction of the fins 6 in such a manner that their ends follow a curved, almost sectional circular, course respectively are located on a corresponding curved, almost sectional circular, line. In this way, focusing of the ultrasonic waves in a plane in the work piece parallel to the surface of the work piece is achieved. Focusing can be selectively influenced by the curvature. Pole assignment in a direction perpendicular to the longitudinal direction of the fins can be carried out as in the preferred embodiment of FIG. 4, i.e. the rows 3 of the permanent magnets are staggered half the width of a magnet from channel to channel in order to achieve a one-sided radiation in the direction indicated by the arrow.

Of course, the ultrasonic transducer described in the preferred embodiments can be extended as desired with regard to the number of fins and channels, HF coils and rows of permanent magnets connected therewith as long as the size of the resulting transducer still permits unequivocal testing of the work piece. Furthermore, for example, the transducer of FIG. 2 may also be designed having a fewer number of rows of permanent magnets, for example, two of these rows.

Even if the dimensions of the permanent magnets, fins and channels are given in the present preferred embodiments, someone skilled in the art may of course choose different dimensions suited for the intended application when building such an ultrasonic transducer.

List of Reference Numbers

1 HF coil
2 permanent magnet
3 row of permanent magnets
4 coil support

-continued

List of Reference Numbers 5 channel
6 fin
7 base plate
8 first HF coil arrangement
9 second HF coil arrangement
10 electric connections
11 face of the fins

What is claimed is:

1. An electromagnetic ultrasonic transducer comprising
a coil support made of a material having magnetic conductivity and having a comb-like structure with at least substantially parallel running channels and fins,
a plurality of first HF coils which are electrically interconnected in series and which are wound on at least some of said fins at a distance from a radiation side of the transducer formed by faces of said fins in such a manner that adjacent coils have an alternating direction of wind, and
means for generating a static magnetic field, wherein said means for generating a static magnetic field includes a plurality of rows of permanent magnets which are disposed in said channels of said transducer in a longitudinal direction of said fins and have an alternating pole assignment.

2. An electromagnetic ultrasonic transducer according to claim 1, wherein said permanent magnets in adjacent channels in a direction perpendicular to the longitudinal direction of said fins alternate in pole assignment.

3. An electromagnetic ultrasonic transducer according to claim 1, wherein said permanent magnets in adjacent channels are disposed toward each other half a width of a magnet in the longitudinal direction of said fins, and further comprising a plurality of second HP coils electrically interconnected in series and wound on some of said fins in a same manner as said first HF coils, with said first coils being wound about a first half of said fins and said second HF coils being wound about a second half of said fins and overlapping said first half of said fins, and if required, one said fin with said first HF coils being separately triggerable from said second HF coils.

4. An electromagnetic ultrasonic transducer according to claim 3, further comprising two high-frequency generators for phase-shifted triggering of said first HF coils and said second HF coils.

5. An electromagnetic ultrasonic transducer according to claim 1, further comprising a plurality of second HF coils interconnected in series are wound in a same manner as said first HF coils on some of said fins, with said first HF coils being wound about a first half of said fins and said second HF coils being wound about a second half of said fins and overlapping said first half, and if required, one said fin with said first HF coils being separately triggerable from said second HF coils, and wherein said permanent magnets in said channels alternate between said fins of said first half and between said fins of said second halt in a direction perpendicular to the longitudinal direction of said fins, with said permanent magnets having a same pole assignment at transition from said first half to said second half in two adjacent channels of said channels in a direction perpendicular to the longitudinal direction of said fins.

6. An electromagnetic ultrasonic transducer according to one of claims 1, 2, 3, 4 or 5, wherein distance of said coils from said radiation side of said transducer is approximately 6–8 mm.

7. An electromagnetic ultrasonic transducer according to one of claims 1, 2, 3, 4 or 5, wherein HF coils for generating ultrasonic waves and HF coils for receiving ultrasonic waves are wound on a common coil support.

8. An electromagnetic ultrasonic transducer according to claim 1 or 3, wherein said rows of permanent magnets are disposed staggered in the longitudinal direction of said fins in such a manner that ends of said rows follow a substantially sectional circular curved course.

9. An electromagnetic ultrasonic transducer according to claim 1 or 3, wherein both said fins and said rows of said permanent magnets are disposed staggered in the longitudinal direction of said fins in such a manner that ends thereof follow a substantially sectional circular curved course.

* * * * *